United States Patent [19]

Laine et al.

[11] Patent Number: 5,418,298
[45] Date of Patent: May 23, 1995

[54] NEUTRAL AND MIXED NEUTRAL/ANIONIC POLYMETALLOOXANES

[75] Inventors: Richard M. Laine; Brian L. Mueller; Tom Hinklin, all of Ann Arbor, Mich.

[73] Assignee: Regents of the University of Michigan, Ann Arbor, Mich.

[21] Appl. No.: 34,531

[22] Filed: Mar. 19, 1993

[51] Int. Cl.$^6$ .................. C08G 79/10; C08G 77/02
[52] U.S. Cl. .................. 525/389; 528/395; 556/443; 556/173; 556/179; 556/9; 556/28; 556/81; 556/27; 556/1; 549/4; 549/3
[58] Field of Search ............ 528/395; 556/443, 173, 556/179, 9, 28, 81, 27, 1; 549/4, 3; 525/389

[56] References Cited

U.S. PATENT DOCUMENTS

| | | | |
|---|---|---|---|
| 2,881,198 | 4/1959 | Bailey et al. | 260/448.8 |
| 3,455,980 | 7/1969 | Frye | 260/448.8 |
| 5,008,422 | 4/1991 | Blum et al. | 556/412 |
| 5,099,052 | 3/1992 | Laine et al. | 556/443 |

OTHER PUBLICATIONS

Frye, C. L. "Pentacoordinate Silicon Derivatives . . . 1,2–Diols" J. Amer. Chem. Soc., 92:5, Mar. 11, 1970 pp. 1205 & 1210.
Frye, C. L. et al. "Pentacoordinate Silicon Compounds V$^{Ia}$ Novel Silatrane Chemistry" J. Amer. Chem. Soc. 93:25 Dec. 15, 1971 pp. 6805–6811.
Blohowiak, K. A. et al., "Synthesis of Penta-Alkoxo and Penta-aryloxy Silicates Directly from $SiO_2$" Inorg. and Organometallic Polymers with Special Properties, 1992 pp. 99–111.
Holmes, Robert R., "The Stereochemistry of Nucleophilic Substitution at Tetracoordinated Silicon", Chem. Review, 1990, vol. 90, No. 1, pp. 17–25.
Swamy, K. C. K., et al., "Pentacoordinate Acyclic and Cyclic Anionic Oxysilicates" A . . . Study$^{1,2}$, J. Amer. Chem. Soc., vol. 112, No. 6, 1990, pp. 2341–2348.
Laine, R. M. et al., "Synthesis of pentacoordinate silicon complexes from $SiO_2$", Nature, vol. 353, Oct. 1991, pp. 642–644.
Blohowiak, K. A. Y., "Synthesis of Penta-alkoxy—and Penta-aryloxy . . . $SiO_2$", Inorganic and Organometallic Polymers With Special Properties, 1992, pp. 99–111.
Chew, K. W. et al., "Inorganic Polymers Derived From Silica and Alumina, An Ion Conducting Polymer from the Reaction of $BaSi(OCH_2CH_2O)_3$ with Tetraethylene Glycol".

Primary Examiner—John C. Bleutge
Assistant Examiner—Margaret W. Glass
Attorney, Agent, or Firm—Brooks & Kushman

[57] ABSTRACT

This invention relates to polymetallooxanes having the moiety:

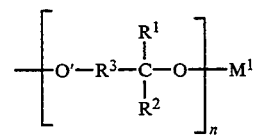

wherein n is 1.5, 2, 3, 4, 5 or 6, $M^1$ is selected from the group consisting of Si, Ge, Sn, Al, Ga, Ti, Zr, or Hf, $R^1$ and $R^2$ are selected from the group consisting of H, OH, $C_{1-8}$ alkyl, $C_{1-6}$ alkoxy, $C_{2-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane or combinations thereof, O' is bonded to $M^1$, another $M^1$ atom, $M^2$ or H, wherein $M^2$ is a group I or II metal of the Periodic Table, and $R^3$ is independently selected from the group consisting of $(CR_2)_y$, $O'—(CR_2CR_2)_yN(CR_2)_y—$, $—(CR_2CR_2)_yN_R(CR_2)_y—$, $O'—[(CR_2CR_2)_yO]_y—(CR_2)_y$, $C_{1-8}$ alkyl, $C_{1-6}$ alkoxy, $C_{2-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane or combinations thereof wherein R is selected from the group consisting of H, OH, $C_{1-8}$ alkyl, $C_{1-6}$ alkoxy, $C_{2-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane or combinations thereof, and wherein y is a number 1 to 10. Also described is a method of producing the claimed polymetallooxanes.

11 Claims, 5 Drawing Sheets

NEUTRAL AND MIXED NEUTRAL/ANIONIC POLYMETALLOOXANES

This invention was made with Government support from the contract DAAL04-91-C-0068 awaded by the Department of the Army. The Government has certain rights in the invention.

TECHNICAL FIELD

This invention pertains to species having M—O—R bonds and a method of making such species from compounds containing M—O—H, M—O—M, M=O and M—O—M' moieties, wherein M or M' may be Si, Ge, Sn, Al, Ga, Ti, Zr or Hf and R is an organic moiety including alkyl, aryl, alkoxy groups, etc. In particular, it pertains to polymeric materials both branched and heterocyclic containing silicon and/or aluminum alkoxides which are suitable for use as precursors for polymers, ceramics, and glasses.

BACKGROUND ART

Metal alkoxides and aryloxides are typically produced by reaction of the metal, or its halide with the respective alcohol, or aryl hydroxy compound or its salt, as illustrated in the following three reactions:

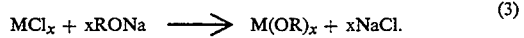

Typically, the metal is made by high temperature carbothermal (1200° C.) or electrochemical reduction of some ore form of that metal such as SiO$_2$ (Kirk-Othemer Encyclopedia of Chemical Technology, 3rd Ed.; WILEY-INTERSCIENCE PUBL., N.Y., New York (1979) Vol. 20, p. 750–880) or bauxite (see "The Production of Inorganic Materials", by De Jonge and Evans, MACMILLAN PUBL., 1990). The chloride is either made simultaneously, or sequentially by treating the metal with chlorine or HCl, as illustrated by:

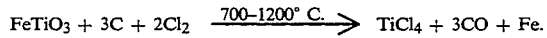

In all of these processes, the pure metal or the halide are formed by high temperature processes which are energy inefficient and polluting. Only after the pure metal or halide are formed by such processes, is it possible to make the metal alkoxide or aryloxide. Thus, the common routes to alkoxides and aryloxides are multi-step and polluting as well as energy and equipment intensive.

As an alternative, the direct chemical synthesis of alkoxides and aryloxides directly from metal oxides offers an opportunity to develop cheaper routes to these materials as well as novel materials. For example, the reaction of silicon with an alkali salt of catechol provides access to the hexaaryloxy dianionic silicon compound:

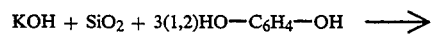

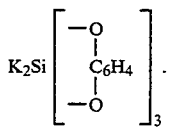

This type of reaction was first reported by Rosenheim et al in 1930 [A. Rosenheim, B. Raibmann, and G. Schendel, Z. Anorg. Chem. 196, 160 (1931)]. Laine et al have also described the preparation of penta- and hexaalkoxysilane anions and dianions. See "Silicon and Aluminum Complexes", R. M. Laine, K. A. Youngdahl and P. Nardi, U.S. Pat. No. 5,099,052, Mar. 24, 1992; and "Barium Tris(1,2ethandiolato)silicate, A Hexacoordinate Alkoxy Silane Synthesized From SiO$_2$." M. L. Hoppe, R. M. Laine, J. Kampf, M. S. Gordon and L. W. Burggraf, Angew. Chem. (in press).

In all instances, these studies only teach the synthesis of anionic silicates with alkali or alkaline earth counterions. In no instance does the prior art teach a commercially viable synthesis of neutral siloxanes, aluminoxanes or polymeric species containing mixtures of neutral and anionic Si and/or Al centers from SiO$_2$ or other siloxy compounds or the equivalent Al species.

U.S. Pat. No. 2,881,198 to D. Bailey and F. O'Connor taught that reacting silica with a catalytic amount of alkali metal under conditions that remove water by distillation or azeotrope (often under pressure) lead to the synthesis of monomeric, neutral alkoxy silanes. However, the disclosed reaction was extremely slow, requiring days to complete. Furthermore, the yields obtained were only 50–78%, as the alkali base used as the catalyst eventually reacted with the SiO$_2$ to produce alkali silicate byproducts.

Frye appeared to teach that silicic acid will react with a large excess of triethanolamine to produce water and what was described as a "more or less nondescript silatrane material". Although the reaction which accompanied this disclosure incorrectly characterized the formula for silicic acid, the synthesis was predicated upon the use of TEA as the sole solvent. Also, the disclosure appears to be limited to relatively low molecular weight oligomeric species. See Frye et al., "Pentacoordinate Silicon Compounds. V. Novel Silatrane Compounds". Journal of Am. Chem. Soc. 93:25; Dec. 15, 1971 p. 6805–6811.

It is an object of this invention to provide neutral and mixed neutral/anionic polymetallooxanes of varying molecular weights so as to be classifiable as monomers, oligomers and polymers. It is a particular object of the present invention to provide such compounds having high molecular weights.

Another object of this invention is to provide a method of making the claimed compounds.

A further object is to provide a method of making neutral and mixed neutral/anionic polymetallooxanes containing alkoxy, aryloxy and alkoxylaryloxy ligands, using catalytic amounts of amines and polyamines to provide commercially viable rates of reaction.

A still further object of the present invention is to provide a method of making ceramic materials having controlled ceramic yield, stoichiometry, phase, microstructure, shape, and surface area, by utilizing the polymetallooxane compounds of the instant invention as ceramic precursors or preceramic materials.

Still another object of the present invention is to provide a method of making ceramic fibers and coatings.

Other objects of the invention include providing methods of making fibers, fine or monodispersed powders, coatings, porous articles such as ceramic foams, filters and membranes, and compression-molded and injection-molded articles using, inter alia, the preceramic polymers as provided herein.

Still other objects of the present invention include methods of using the polymetallooxane polymers of the invention as binders, as adhesives, in infiltration applications (as in wood preservation), and in matrix and composite materials.

Additional features of the invention will be set forth in the description which follows and will become apparent to those skilled in the art on examination of the following, or may be learned by practice of the invention.

SUMMARY OF THE INVENTION

Figure 1:
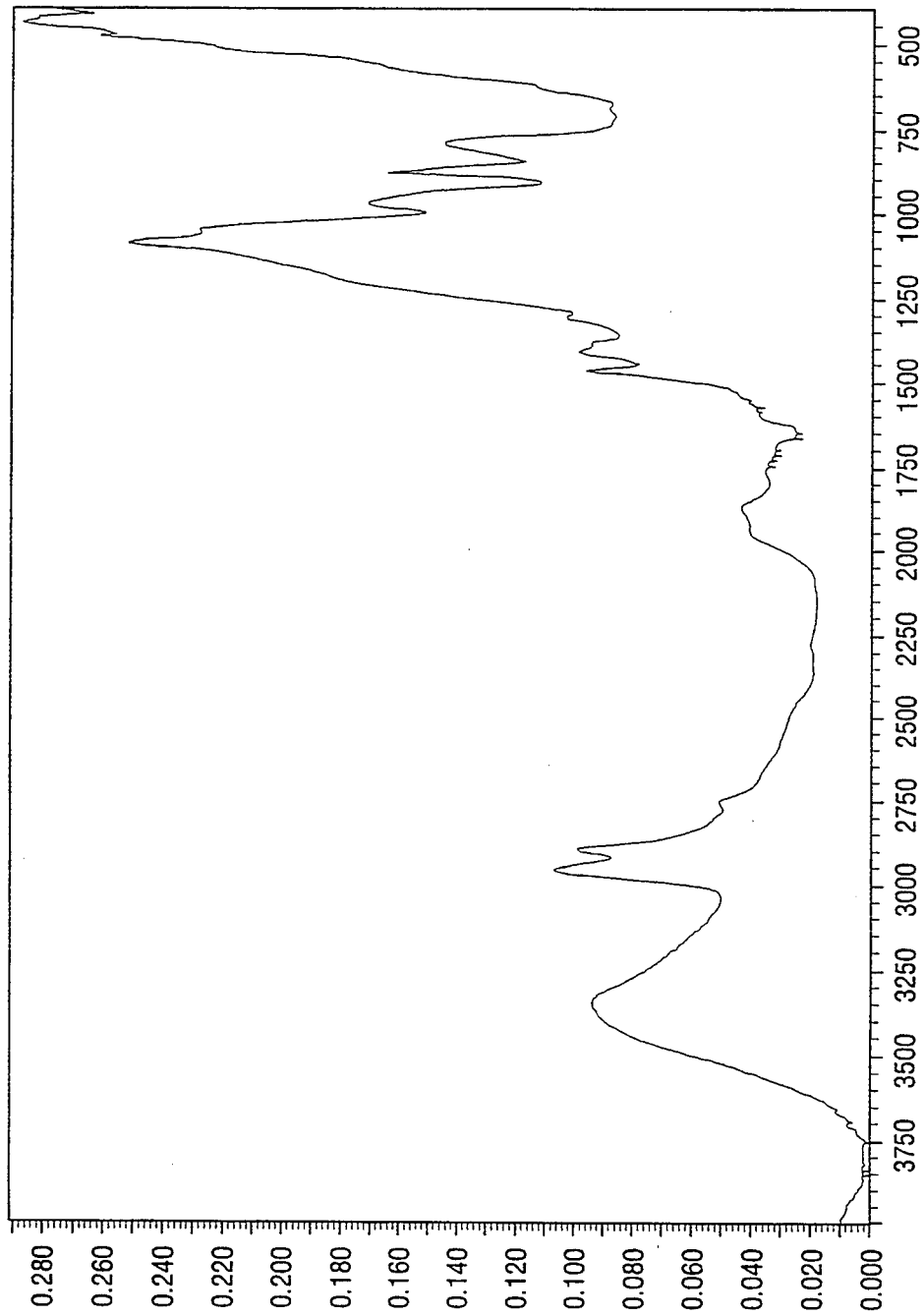
FIG. 1 is an FTIR spectrograph illustrating a plot of Absorbance vs. Wave Number for the reaction product of Example 4.

A polymetallooxane comprising the moiety:

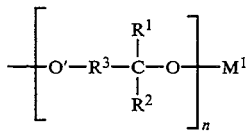

wherein n is 1.5, 2, 2.5, 3, 4, 5 or 6;

$M^1$ is selected from the group consisting of Si, Ge, Sn, Al, Ga, Ti, Zr, or Hf;

$R^1$ and $R^2$ are independently selected from the group consisting of wherein R is selected from the group consisting of H, OH, $C_{1-8}$ alkyl, $C_{1-6}$ alkoxy, $C_{1-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane or combinations thereof;

O' is bonded to $M^1$, another $M^1$ atom, $M^2$ or H, wherein $M^2$ is selected from the group consisting of Si, Ge, Sa, Al, Ga, Ti, Zr, or a group I or II metal of the Periodic Table; and $R^3$ is independently selected from the group consisting of $(CR_2)_{y'}$, $O'(CR_2CR_2)_yN(CR_2)_{y-}$, $-(CR_2CR_2)_yNR-(CR_2)_{y-}$, $O'[(CR_2CR_2)_yO]_{y-}(CR_2)_y$, $C_{1-8}$ alkyl, $C_{1-16}$ alkoxy, $C_{1-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane or combinations thereof wherein R is selected from the group consisting of H, OH, $C_{1-8}$ alkyl, $C_{1-6}$ alkoxy, $C_{1-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, C1-10 alkylsiloxane or combinations thereof. and wherein y is a number from 1 to 10.

Optionally, each $R^1$, $R^2$, $R^3$, or R group may further contain one or more atoms selected from the group consisting of Si, Ge, Sn, Al, Ga, Ti, Zr, Hf, or a Group I or II metal.

Also described is a polymetallooxane comprised of branched moieties such as $[(O-R^1-OH)_xM(O-R^2-O)_y]Z$ where M is Si, Ge, Sn, Al, Ga, Ti, Zr, Hf or a Group I or II metal; $R^1$ and $R^2$ may be the same or different and are selected from the group consisting of $C_{1-8}$ alkyl, $C_{1-16}$ alkoxy, $C_{1-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane or combinations thereof; Z us selected from the group consisting of Si, Ge, Sn, Al, Ga, Ti, Zr, Hf, the Group I metals, the Group II metals, or the residue of an amine reactant; and x and y may be the same or different and are numbers from 1 to 10.

Also described is a polymetallooxane material containing the heterocyclic moiety:

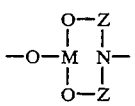

wherein M may be Al or Si, and Z is a residue of an amine reactant. Upon exposure to temperature sufficient to cause pyrolysis the claimed material will serve as a ceramic precursor or preceramic and will produce a ceramic material in commercially feasible yields.

Also described is a method of producing the claimed polymeric polymetallooxane by reacting an aluminoxy or siloxy containing material together with an amine and a polyol and heating the resulting mixture to a temperature sufficient to remove at least a portion of water produced during the reaction and recovering the polymetallooxane produced.

DESCRIPTION OF PREFERRED EMBODIMENTS

In the preparation of the polymeric polymetallooxanes described herein compounds having the functional moieties M—O—H, M—O—M, M=O, and M—O—M' moieties will be used as starting reactants. M may be selected from the group consisting of Si, Ge, Sn, Al, Ga, Ti, Zr or Hf. Preferably, the starting reactant will contain Al or Si and, most preferably, in the form of aluminoxy or siloxy functional groups. Suitable siloxy or aluminoxy containing materials that may be used are any sands, ore, and the like, that would provide aluminum hydroxide, alumina or silicon dioxide or other silicon oxide containing materials. All that is desired is that the siloxy ore or the aluminoxy containing material be reactive with the polyol/amine mixtures described below to produce the desired polymeric polymetallooxane materials.

The term "polymeric" as used herein is intended to encompass both low and high molecular weight structures, such that monomers, oligomers and high molecular weight polymers are within the scope of the claimed polymetallooxane compositions. The M atom may be present in the desired materials in branched moieties or heterocyclic moieties or both.

The amines that will be preferably utilized in the present invention can be selected from a wide variety of nitrogen containing materials. Most preferably, however, the amine utilized herein will have a high boiling point. High boiling amines, polyamines or aminols may be used. Of these, polyamines and aminols are most preferred since they provide a higher base strength. For example, simple —$C_2$ to $C_{10}$ amines and polyamines may be utilized such as primary, secondary and tertiary amines, where the substituents are preferably methyl, ethyl or lower alkyl groups. The amine substituents can be essentially any other organic radical, so long as they do not interfere with the desired reaction. Hydrogen, benzyl, alkoxyalkyl, and the like are illustrative examples. Divalent organic groups, such as alkylene or substituted-alkylene, e.g. oxyalkylene or poly(oxyalkylene), or, less desirably, arylene, alkarylene or substituted arylene can also be used. Unsaturated groups, e.g., alkylene groups such as —CH=CH— or

also be used wherein R may be one of the substituent groups discussed immediately above. Other possible R groups include cyclic or aromatic groups; one type of useful amine, for instance, is represented by the formula:

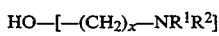

where x is 1 to 3 and $R^1$ and $R^2$ are as discussed immediately above. Other examples of suitable polyamines include diethylene triamine, triethylenetetraamine, and tetraethylene pentamine. Dialkanolamines, of the general formula $RN(ROH)_2$, and trialkanolamines, of the general formula $N(ROH)_3$, are also useful wherein R is generally as discussed above. Cyclic amines having formulas such as the following may also be used:

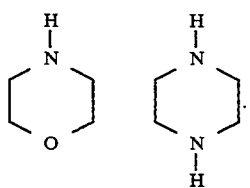

Some specific examples of suitable amines are as follows:
dimethylethanolamine
dimethylpropanolamine
dimethylisopropanolamine
dimethylbutanolamine
diethylethanolamine
methylethanolamine
N-benzylethanolamine
diethanolamine
triethanolamine
triethylenetetraamine
dimethylaminomethyl phenol
tris(dimethylaminomethyl)phenol
2-[2-(dimethylamino)ethoxy]ethanol
1-[1-(dimethylamino)-2-propoxy]-2-propanol
2-(2-[2-(dimethylamino)ethoxy]ethoxy)ethanol
102[(dimethylamino)ethoxy]-2-propanol
1-(1-[dimethylamino]-2-propoxy]-2-propoxy)-2-propanol
tributyl amine, trioctyl amine (1,2 and 1,3) diamino, propanol, hexane diamine, butane diamine, as well as tri and tetra amino oligomers and polymers.

The most preferred amines are triethanolamine (TEA), triethylenetetraamine (TETA) and mixtures thereof.

It is to be appreciated that low or high molecular weight polyamines may also be utilized such as those that are based on polyethyleneimine and the like.

It is also most preferred that the reaction to produce the claimed polymetallooxane polymeric materials described herein take place in the presence of reactive solvents such as hydroxy-containing solvents. Suitable solvents are a variety of alcohol-containing materials such as $C_2$ to $C_{10}$ mono, di, or trialcohols such as ethanol, propanol, as well as ethylene glycol, propanediol, glycerol, and the like.

The most preferred reactive solvents for use in the instant invention are the 1,2 and 1,3 diols. Of these, ethylene glycol is most preferred.

It is also desirable to utilize non-reactive solvents, such as oxygen-containing solvents which are widely available as ether-containing solvents.

Preferred non-reactive solvents are monoalkyl or dialkyl ethers of ethylene glycol, diethylene glycol, triethylene glycol, or tetraethylene glycol and the acetate derivatives thereof. The alkyl group preferably ranges from 1 to 4 carbon atoms. The use of such non-reactive solvents may be advantageous with respect to the high cost and low availability of some reactive solvents, particularly some preferred diols. Illustrative examples of suitable non-reactive solvents include a crown ether, diethoxy-diethylene glycol or polyether such as polyethylene glycol.

Exemplary materials are Cellosolve (trademark of Union Carbide for monoethyl ether of ethylene glycol), methyl Cellosolve, butyl Cellosolve, isobutyl Cellosolve, hexyl Cellosolve, Carbitol (trademark of Union Carbide for monothyl ether of diethylene glycol), butyl Carbitol, hexyl Carbitol, monobutyl ether of propylene glycol, monopropyl ether of propylene glycol, monomethyl ether of propylene glycol, monomethyl ether of dipropylene glycol, butoxytriglycol $C_2H_5O(C_2H_4O)_3H$, 1, butoxyethoxy-2-propanol, diethylene glycol, triethylene glycol, tetraethylene-glycol, propylene glycol, dipropylene-glycol, tripropylene glycol, polypropylene glycol, having a molecular weight up to about 2000, hexylene glycol, 2 ethyl-1, 3-hexane diol; 1,5-pentane diol, ester diol-204(2,2-dimethyl-3-hydroxypropyl 2,2-dimethyl-3-hydroxyl propionate), and the like.

The reaction temperature to produce the claimed polymers can vary depending upon the reagents that are utilized. An operative consideration is that as the reaction proceeds, water must be removed, preferably by distillation. Generally, the temperature and pressure will be adjusted so that the amine will remain in the liquid phase, while the water will be removed. Accordingly therefore, when the reaction is operated at atmospheric pressure, the temperature will range from approximately 100° C. up to 250° C. Alternatively, if an azeotrope mixture is utilized and the reaction run at atmospheric pressure, the temperature is decreased since azetropes generally boil at lower temperatures. Correspondingly, if the pressure is less than atmospheric pressure, that is, if a partial vacuum is applied, the reaction temperature necessary to remove water will likewise be less.

If the polymetallooxane monomers, oligomers and polymers that are obtained according to the claimed invention contain a heterocyclic moiety, it is preferred that the moiety comprise the structure:

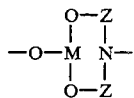

wherein M is selected from the group consisting of Si, Ge, Sn, Al, Ga, Ti, Zr or Hf and is most preferably Si or Al, and Z is a residue of the amine reactant discussed above. Note, however, that not all heterocycle moieties will contain a dative bond; i.e. an N—M bond.

When Z incorporates portions of the reactive solvent, Z will not bond to N, with the exception of hydrogen bonds.

When M is Si, the compounds resulting from the claimed invention will not necessarily contain the heterocyclic amine residue moiety discussed above. Branched polymeric compounds having structures such as [HO—CH$_2$CH$_2$O—]$_2$—[Si—OCH$_2$CH$_2$O] are also possible. Other examples are:

combinations thereof; Z us selected from the group consisting of Si, Ge, Sn, Al, Ga, Ti, Zr, Hf, the Group I metals, the Group II metals, or the residue of an amine reactant; and x and y may be the same or different and are numbers from 1 to 10.

The branched siloxane polymer as exemplified by the above structures, can vary in molecular weight as a consequence of several parameters including the polyol used, the temperature, the concentration and the presence of base or acid. At low concentrations of amine the degree of crosslinking in the polymeric polymetallooxane will be decreased. Also, the use of simpler diols, such as ethylene glycol, favors lower crosslink densities. The use of triols and higher functionality polyols will generally increase the degree of crosslinking, however, simple triols may actually form very stable ring structures, e.g. triethanolamine. Higher temperatures will promote increased crosslinking through the reaction of the danging R—OH of the branches which leads to higher viscosities in the resulting polymeric polymetallooxane. Higher concentrations of amine will enhance the likelihood of dangling R—OH in the branches, reacting to form a greater or higher degree of crosslinking which leads to higher viscosities in the product. Finally, the use of TETA leads to products with more branching as compared to the use of TEA

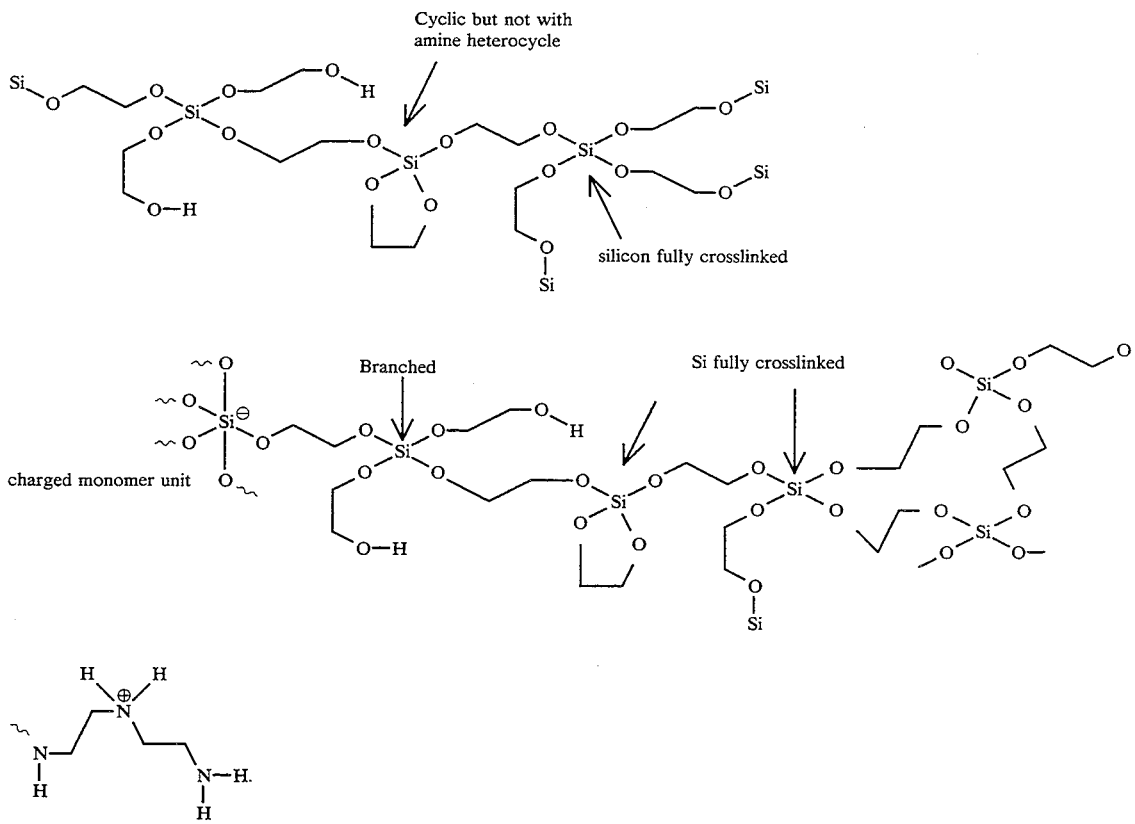

The polymetallooxanes having branched moieties may be characterized as [(O—R$^1$—OH)$_x$M(O—R$^2$—O)$_y$]Z where M is Si, Ge, Sn, Al, Ga, Ti, Zr, Hf or a Group I or II metal; R$^1$ and R$^2$ may be the same or different and are selected from the group consisting of C$_{1-8}$ alkyl, C$_{1-16}$ alkoxy, C$_{1-8}$ alkene, C$_{6-12}$ aryl, C$_{1-8}$ hydroxyalkyl, C$_{1-8}$ thioalkyl, C$_{2-12}$ alkoxyalkyl, C$_{4-20}$ heteroaromatic, C$_{1-10}$ alkylsilane, C$_{1-10}$ alkylsiloxane or which promotespolymetallooxane products with the heterocycle moiety as discribed above.

It is also to be appreciated that the polymetallooxane monomers, oligomers and polymers that are obtained can contain various cyclic moieties wherein the number of members of the ring can range from 5 to 9. An illustrative example is:

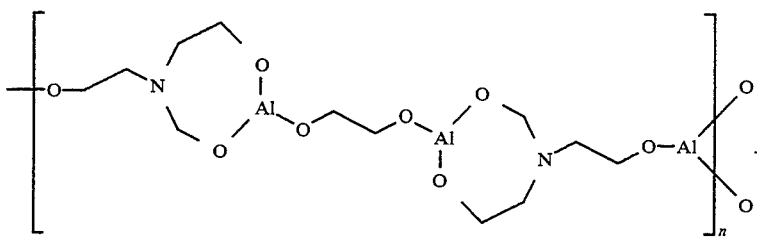

Additional ring structures that may be present are those having the moiety shown below wherein Z is as defined above:

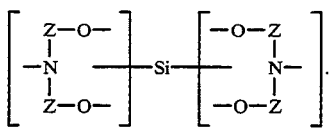

After the polymeric materials are obtained, they may be heated to a temperature sufficient to cause pyrolysis to obtain the desired end products such as ceramics.

The present case is most preferably concerned with the synthesis of neutral or mixed ionic and neutral glycolato silicates, aluminates, and aluminosilicates from $SiO_2$, aluminum oxide and hydroxide [$Al_2O_3$ or $Al(OH)_3$], or mixtures of these oxides with ethylene glycol and a high boiling amine such as triethanolamine.

Most preferably, the case is concerned with a method of dissolving $SiO_2$, aluminum oxide and hydroxide [$Al_2O_3$ or $Al(OH)_3$], or mixtures of these oxides (in any molar ratio) in the absence of or in the presence of alkaline or alkali metal hydroxides or oxides in ethylene glycol (or other 1,2 or 1,3 diol or polyol) and removal of product water in the presence of either stoichiometric or catalytic amounts of a high boiling amine, oligoamine or polyamine or aminol, or oligoamino-alcohols.

The products of these reactions with catalytic amounts of amine are neutral, branched alkoxy polymetallooxane complexes or polymers. In the presence of slightly less than stoichiometric or stoichiometric amounts of amine to metal ion, the products are either neutral or mixed neutral/anionic and may be either branched or heterocycle containing. While not wishing to be bound to any particular theory, it is believed that the addition of alkali or alkaline earth metals containing materials cause the formation of mixed neutral/anionic complexes or polymers. The rheological and chemical properties of the desired products can be controlled by the type of diol present, the reaction conditions and the amount and type of catalyst added as discussed above.

For example, if 10 mol % of amine as a catalyst is added as described below with minimal distillation of solvent (sufficient to dissolve $SiO_2$) then the resulting solution will have minimal viscosity and would be ideal for some coatings applications (for polymer or ceramic, abrasion resistant coatings) and for reducing the flammability of wood. It would also be an ideal precursor for sol-gel processing (e.g. for aerogels).

If the solvent is reduced by further distillation under either ambient conditions or a vacuum, then the viscoelastic properties of the product increase. If enough solvent is removed, further crosslinking is obtained and a meltable, castable polymer is obtained. The properties of the product may range from a high temperature liquid crystalline polymer (e.g. where the diol is catechol and/or hydroquinone) to a flexible, scratch-resistant polymer/ceramic composite.

It has also been found that the claimed polymeric polymetallooxanes are particularly advantageous when used as ceramic precursors or preceramics. Hydrolysis with subsequent or simultaneous heating of the above polymetallooxane polymers, especially of the Si/Al materials could provide zeolitic materials or aerogels depending on the workup. Pyrolysis of 2:6 mixtures of Si:Al copolymers produced as described herein will provide mullite powders at temperatures as low as 800°–1200° C.

Still further removal of solvent, particularly the glycol materials, could provide a soluble, high temperature melting ceramic precursor, suitable for use in spinning fibers of silica, alumina, mullite or cordierite, and the like. These preceramic polymetallooxane polymers can be used by themselves or might be mixed with small amounts of organic polymer spinning aids to improve spinnability. These are readily amenable to nitriding by exposure to $NH_3$ at temperatures about or above 500° C.

Polymetallooxane as used herein is intended to describe compounds which contain multiple metal-oxygen-carbon bonds per metal center. Preferably such compounds will have from three to six such bonds. In the instances where an oligomer or polymer is formed and some of the metal centers in the polymer are anionic, the counterions are ammonium species or Group I or II metals. The nitrogen of the amine and/or ammonium species associated with the anionic metal centers is not required to bond to the metal center, although, this may occur for some specific amines and/or metals.

For example, if triethylene tetraamine is used as a catalyst, it can, at low temperatures cause some anionic metal centers to form and will act as an ammonium counterion. These compounds are typically not stable on heating. However, if triethanolamine is used as a catalyst, some of the oligomers may contain triethanolamine as a ligand where the nitrogen may form a dative bond to silicon. Thus, the polymetallooxanes of the instant invention are not classifiable as silatranes since dative bonds between N and M are optional rather than mandatory.

"High molecular weight" polymers as provided herein are polymers that have an $M_n$ greater than about 10,000 Da, in some cases greater than about 20,000 Da, and an $M_w$ greater than about 30,000 Da and in some cases, greater than 100,000 Da. $M_n$ and $M_w$ have their standard definitions of number-average molecular weight and weight-average molecular weight.

"Substantially linear" oligomers or polymers as used herein are noncyclic structures having two or more monomeric units and which are not extensively crosslinked, where the monomeric units may contain small cyclic moieties. For example, in the triethylene tetramine catalyzed dissolution of silica, the following type of "substantially linear" oligomers have been identified:

temperatures as low as 100° C. It is also possible to run the reaction at temperatures below 100° C. at reduced pressure, or with a solvent that can be used to remove

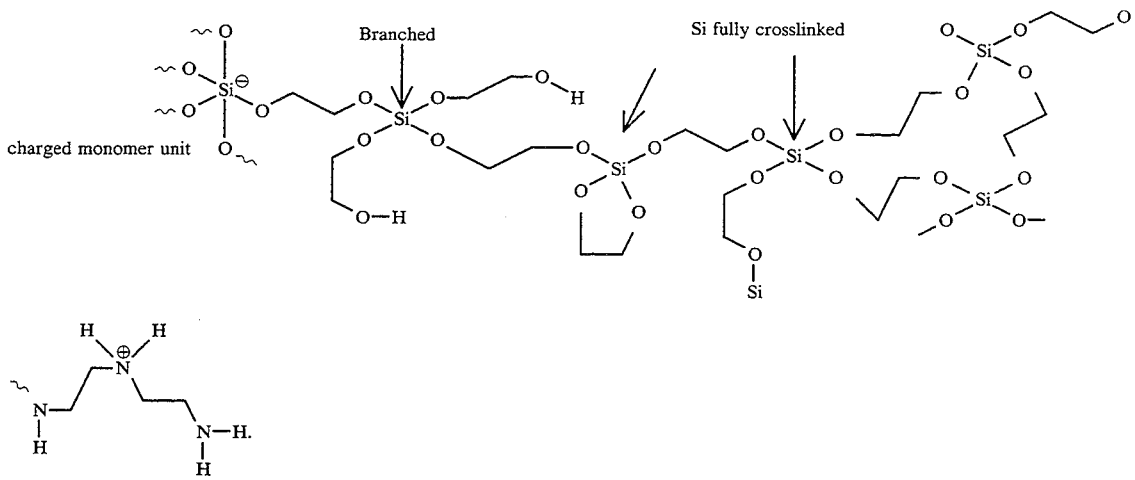

In another example, in the triethanolamine catalyzed dissolution of aluminum hydroxide, the following type of "substantially linear" oligomers have been identified. Note that in this instance, a cyclic monomer is part of the polymer structure:

the water by azeotrope. Thus, ethanol can also be used as solvent. Silica can be dissolved with TETA in ethanol at a reaction temperature of 72° C.

The tradeoff is that at lower reaction temperatures, the kinetics of the reaction are slower and reactions may

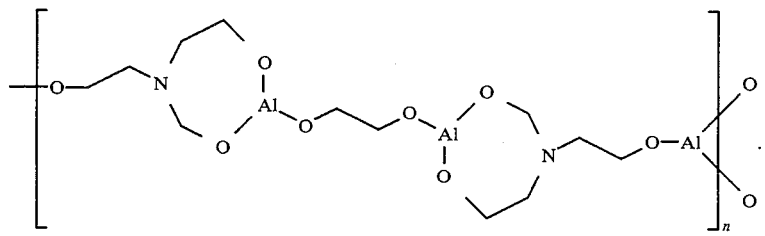

A "substantially pure" ceramic material is intended to mean a ceramic material comprising at least 75% of a particular compound. For example, the polymer made by mixing the following; 2MgO: 2Al$_2$O$_3$: 5SiO$_2$ in a slight stoichiometric deficiency of triethanolamine and excess ethylene glycol followed by distillative removal of excess ethylene glycol and water produces a polymer which, upon heating to 1000° C. for one to two hours, and most preferably, two hours, produces a 42% ceramic yield. This resulting ceramic material converts to phase pure cordierite [2MgO.2Al$_2$O$_3$.5SiO$_2$] upon further heating to temperatures of about 900° C. or more in an oxygen containing atmosphere.

A "rheologically useful" polymer is defined as one which is meltable, soluble or malleable or deformable such that shapes can be formed from the polymetallooxane polymer.

The claimed reaction is carried out under nitrogen or air, in solution, with the solvent compris- TETA, it is most preferred that much less than one equivilent of nitrogen be used.

The reaction is run so as to drive off water which is produced during the reaction process. To do this, it is preferable to create conditions wherein the reaction is run above the boiling point of water. With ethylene glycol, the preferred reaction temperature is 200° C., the boiling point of ethylene glycol. However, by using a partial vacuum, it is possible to run this reaction at take weeks to complete. Thus, the range of reaction temperatures may be from 50°–290°, but preferably from 100°–220° C. and most preferably from about 130°–200° C.

While having described the invention above, listed below herein are preferred embodiments of the invention wherein all temperatures are in degrees Centigrade and parts are parts by weight unless otherwise indicated.

EXAMPLE 1

Dissolution of SiO$_2$ using N(CH$_2$CH$_2$OH)$_3$-triethanolamine

Silica (11.55 g of 600 mesh, 192 mmol) was put into a 500 mL Schlenk flask with a stirbar. To the flask was added, slightly less than one equivalent of triethanolamine (28.0 g or 187 mmol) and 320 mL of ethylene glycol (EG). The slurry was then heated under N$_2$ to distill off excess ethylene glycol coincident with H$_2$O produced during the reaction. During the course of the reaction, 250 mL of distillate was recovered. The reaction was run for 12 h to give a clear, slightly yellow solution. Removal of remaining solvent first gives a slightly yellow viscous oil that eventually forms a clear, crosslinked polymer.

EXAMPLE 2

Dissolution of SiO2 using N(CH2CH2OH)3-triethanolamine

Silica (10.77 g of 600 mesh, 180 mmol) was put into a 500 mL Schlenk flask with a stirbar. To the flask was added one third of an equivalent of triethanolamine (8.5 g or 57 mmol) and 310 mL of EG. The slurry was then heated under $N_2$ to distill of excess ethylene glycol coincident with $H_2O$ produced during the reaction. During the course of the reaction, 420 mL of distillate was recovered. 250 mL additional EG was added during the course of the reaction. The reaction was run for 24 h to give a clear, slightly yellow solution. Removal of remaining solvent gave a slightly yellow oil that became a clear, crosslinked polymer on removal of remaining EG.

EXAMPLE 3

Dissolution of SiO2 using N(CH2CH2OH)3-triethanolamine

Silica (10.40 g of 600 mesh, 173 mmol) was put into a 500 mL Schlenk flask with a stirbar. To the flask was added 0.1 equivalent of triethanolamine (2.58 g or 17 mmol) and 310 mL of ethylene glycol (EG). The slurry was then heated under $N_2$ to distill off excess ethylene glycol coincident with $H_2O$ produced during the reaction. During the course of the reaction, 350 mL of distillate was recovered. 250 mL additional EG was added during the course of the reaction. The reaction was run for 12 h to give a clear solution. Removal of remaining solvent gave a clear, viscous oil that became a clear, crosslinked polymer on removal of remaining E.

EXAMPLE 4

Dissolution of SiO2 using NH2[CH2CH2NH]3H-triethylenetetraamine

Silica (10.40 g of 600 mesh, 173 mmol) was put into a 500 mL Schlenk flask with a stirbar. To the flask was added 0.1 equivalent of triethylene tetraamine (2.58 g or 17 mmol) and 310 mL of ethylene glycol (EG). The slurry was then heated under $N_2$ to distill of excess ethylene glycol coincident with $H_2O$ produced during the reaction. During the course of the reaction, 350 mL of distillate was recovered. 250 mL additional EG was added during the course of the reaction. The reaction was run for 12 h to give a clear solution. Removal of remaining solvent gave a clear, viscous oil that became a clear, crosslinked polymer on removal of remaining EG.

$^{29}$Si NMR of the solution gave four peaks at approximately $-78$, $-79$, $-80$, $-81$ ppm corresponding to species of the type:

Si(OCH2CH2OH)4, ($\mu$-OCH2CH2O)Si(OCH2CH2OH)3, ($\mu$OCH2CH2O)2—Si(OCH2CH2OH)2, and ($\mu$-OCH2CH2O)3Si(OCH2CH2OH), Si($\mu$OCH2CH2O)4 and
(OCH2CH2O)Si(OCH2CH2OH)2, ($\mu$-OCH2CH2O)-(OCH2CH2O)Si(OCH2CH2OH),
($\mu$-OCH2CH2O)2Si(OCH2CH2O. In this instance, $\mu$- means that the ethylene glycol unit is bridging two silicon centers as opposed to binding twice to the same silicon.

These NMR peaks do not indicate the presence of pentacoordinate silicon.

Figure 2:
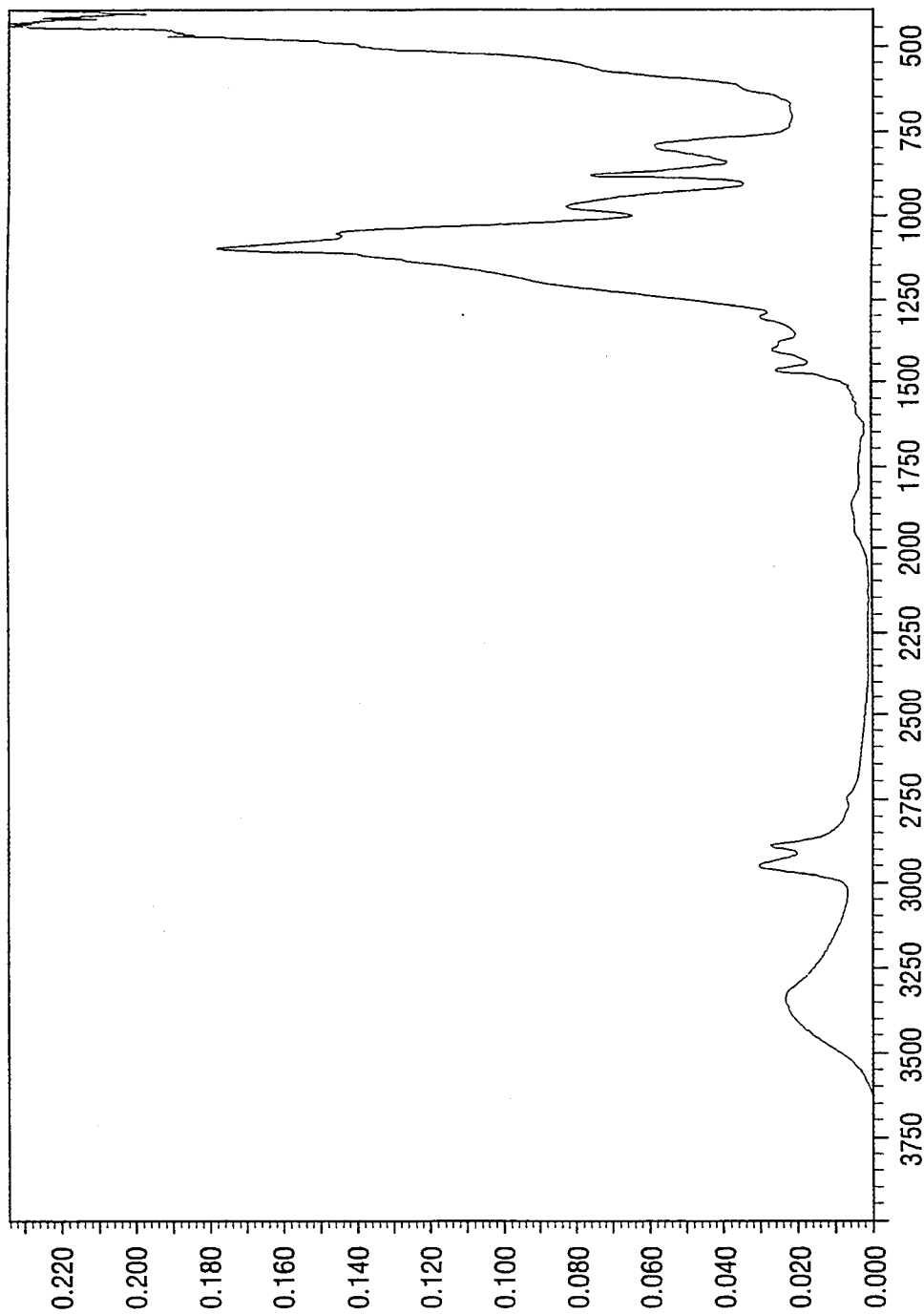
FIG. 2 is a second FTIR spectrograph plotting the Diffuse Reflectance vs. Wave Number for the reaction product of Example 4.

Turning to FIG. 1, an FTIR analysis of the reaction product is shown, illustrating Absorbance vs. Wave Number. FIG. 2 is a second FTIR analysis illustrating Diffuse Reflectance vs. Wave Numbers. The products were vacuum dried for two hours at 225° C. and the samples prepared and analyzied using conventional FTIR analytical techniques. The paper by Blohowiak, K. A. Y.; Hoppe, M. L.; Chew, K. W.; Mueller, B. M.; Scotto, C. S.; Hinklin, T.; Babonneau, F.; Kampf, J.; R. M. submitted to J. AM. CHEM. SOC. is hereby incorporated by reference.

FABS analysis did not lead to the identification of any volatile species; however, introduction of TEA at room temperature depolymerized the material and gave product identifiable by FABS as the same as those obtained when TEA is used as a catalyst.

EXAMPLE 5

Dissolution of SiO2 using triethylenetetraamine NH2[CH2CH2NH]3H

Silica (10.0 g of 600 mesh, 166 mmol) was put into a 500 mL Schlenk flask with a stirbar. To the flask was added a slight excess of one equivalent of triethylene tetraamine (23.5 mls of a 60% solution or 156 mmol) and 300 mL of ethylene glycol. The slurry was then heated under $N_2$ to distill of excess ethylene glycol coincident with $H_2O$ produced during the reaction. During the course of the reaction, 250 mL of distillate was recovered. The reaction was run for 12 hours to give a clear bright yellow solution. The viscous solution was then washed three times with 100 mls of acetonitrile to wash away excess glycol to afford a fine white powder.

EXAMPLE 6

Dissolution of SiO2 using triethylenetetraamine NH2[CH2CH2NH]3H

Silica (10.0 g of 600 mesh, 166 mmol) was put into a 500 mL Schlenk flask with a stirbar. To the flask was added 0.1 equivalent of triethylenetetraamine (16 mmol) and 300 mL of ethylene glycol. The slurry was then heated under $N_2$ to distill of ethylene glycol coincident with $H_2O$ produced during the reaction. During the course of the reaction, 250 mL of distillate was recovered. The reaction was run for 12 hours to give a clear bright yellow solution. The viscous solution was then washed three times with 100 mls of acetonitrile to afford a fine white powder.

EXAMPLE 7

Dissolution of SiO2 and Al(OH)3xH2O using NH2[CH2CH2NH]3H triethylenetetraamine Silica (10.0 g of 600 mesh, 166 mmol) was put into a 500 mL Schlenk flask with a 0.1 metal equivalent aluminum hydroxide hydrate (50–57% as $Al_2O_3$, 2.6 g, 2 mmol). To the flask was added a slight excess of one equivalent of triethanolamine (24.25 mls 183 mmol) and 300 mL of ethylene glycol. The slurry was then heated under $N_2$ to distill of ethylene glycol coincident with $H_2O$ produced during the reaction. During the course of the reaction, 250 mL of distillate was recovered. The reaction was run for 12 hours to give a slightly yellow-brown solution.

EXAMPLE 8

Dissolution of SiO2 and Al(OH)3xH2O using triethanolamine N(CH2CH2OH)3

Silica (1.5 g of 600 mesh, 25 mmol) was put into a 500 mL Schlenk flask with one metal equivalent aluminum hydroxide hydrate (50–57% as Al₂O₃, 2.6 g, 25 mmol). To the flask was added a slight excess of one equivalent of triethanolamine (24.25 mls 183 mmol) and 300 mL of ethylene glycol. The slurry was then heated under N₂ to distill of ethylene glycol coincident with H₂O produced during the reaction. During the course of the reaction, 250 mL of distillate was recovered. The reaction was run for 12 hours to give a slightly yellow-brown solution.

EXAMPLE 9

Dissolution of Al(OH)₃xH₂O using triethanolamine N(CH₂CH₂OH)₃

Al(OH)₃ x H₂O (50–57% as Al₂O₃) (30.9 g, 322 mmol of Al) is placed in a 500 ml Schlenk flask along with 45 g of triethanolamine (300 mmol). 250 ml of ethylene glycol is added and the slurry was heated to distillation temperature under N₂. Ethylene glycol and water are distilled from the reaction mixture to drive the reaction to completion. The solution goes clear after about 4 hours of distillation. This solution is used as a polymer precurser to aluminum containing ceramics. The oligomers and polymers formed were identified by FABs mass spectroscopy as noted in the analyses below.

EXAMPLE 10

Figure 3:
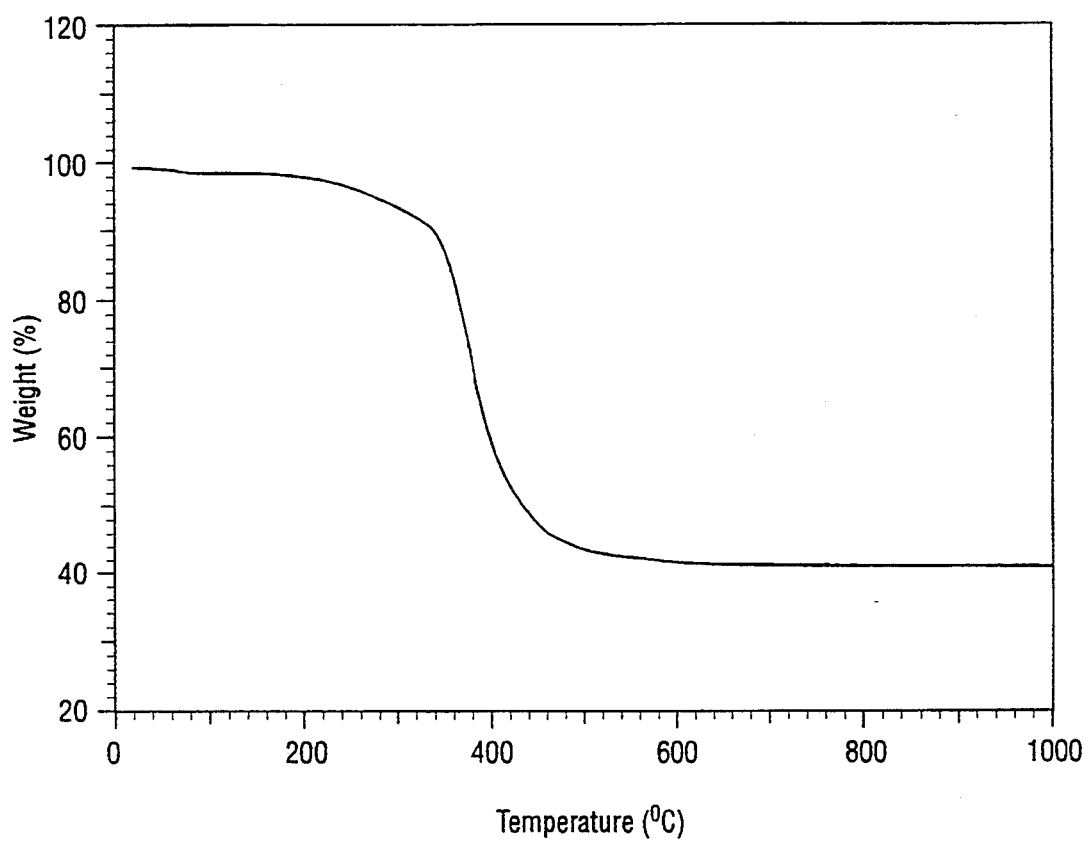
FIG. 3 shows the TGA analysis of the cordierite precursor of Example 10.
Figure 4:
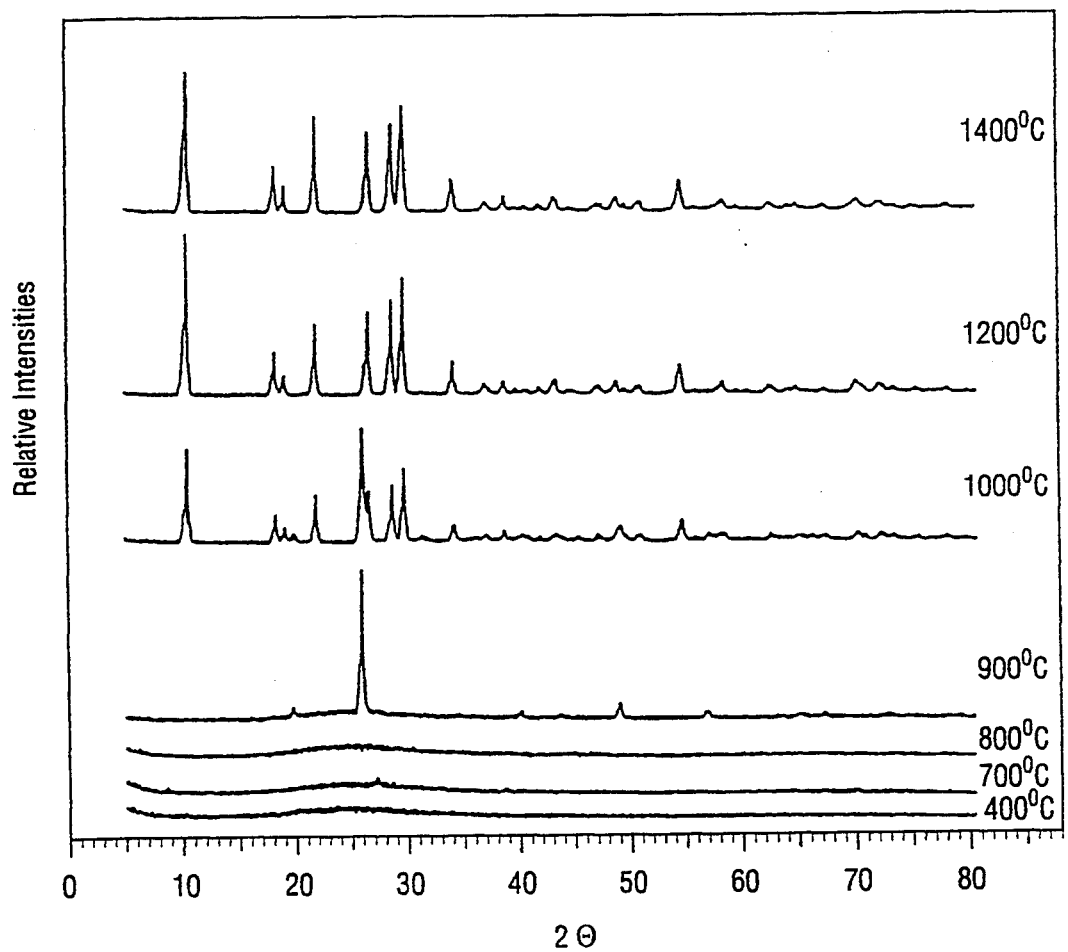
FIG. 4 illustrates the results of X-ray diffraction analysis of the same cordierite precursor after heating to temperatures from 900° C. to 1400° C.

Dissolution of a cordierite [2MgO.2Al₂O₃.5SiO₂] mixture of MgO/Al(OH)₃xH₂O/SiO₂ using triethanolamine Al(OH)₃ x H₂O (50–57% as Al₂O₃) (30.9 g, 322 mmol of Al) is placed in a 500 ml Schlenk flask along with 50 g of triethanolamine (300 mmol). 250 ml of ethylene glycol is added and the slurry was heated to distillation temperature under N₂. Ethylene glycol and water are distilled from the reaction mixture to drive the reaction to completion. To this solution are added 500 ml of additional ethylene glycol, 24.18 g SiO₂ (402 mmol) and 6.83 g MgO (322 mmol of 95% ceramic yield MgO). The solution is again heated to distillation and glycol and water are removed by distillation until the solution is clear. The solution is removed under reduced pressure to give a hard, glassy polymer precursor. This brittle polymer is ground by mortar and pestle in the glovebox to give a clear tan solid. The TGA analysis of FIG. 3 shows reproducibility in that the ceramic yield is always 39–42%. On pyrolysis to 900° C., the product is phase pure μ-cordierite as established by the XRD analysis of FIG. 4.

EXAMPLE 11

Dissolution of a cordierite mixture of MgO/Al(OH)₃xH₂O/SiO₂ using triethanolamine Al(OH)₃ x H₂O (50–57% as Al₂O₃) (30.9 g, 322 mmol of Al), 24 g SiO₂ (402 mmol) and 6.8 g MgO (322 mmol of 95% ceramic yield MgO) are placed in a 500 ml Schlenk flask along with 50 g of triethanolamine (335 mmol) and 300 mL of ethylene glycol. The mixture is heated to distillation which is continued, with readdition of dry ethylene glycol, until the entire solution goes clear. This requires from 4 to 24 h depending on stirring and exact heating temperature. The chemical and ceramic analyses are identical to the results of Example 10.

EXAMPLE 12

Dissolution of a spinel mixture of MgO/Al(OH)₃xH₂O using triethanolamine

Al(OH)₃ x H₂O (50–57% as Al₂O₃) (30 g, 320 mmol of Al), and 3.4 g MgO (160 mmol of 95% ceramic yield MgO) are placed in a 500 ml Schlenk flask with 50 g of triethanolamine (335 mmol) and 300 mL of EG. The mixture is distilled, with readdition of dry ethylene glycol, until the entire solution goes clear. This requires from 8 to 24 h depending on stirring and exact heating temperature.

Figure 5:
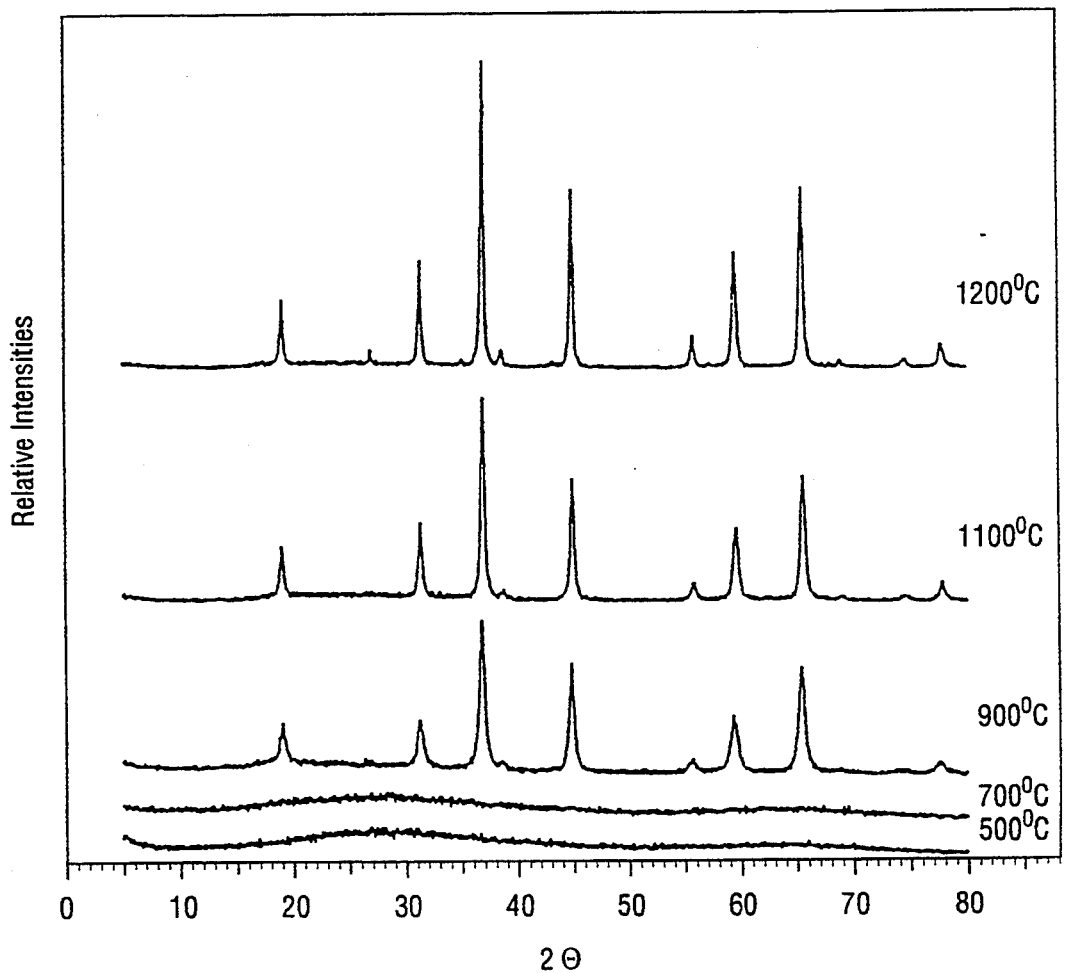
FIG. 5 is an X-ray diffraction analysis of the spinel precursor of Example 12 after heating to temperatures from 900° C. to 1200° C.

The chemical formula of the coordierite precursor is suggested to be Mg₂Si₅(OCH₂CH₂O)₁₂.Al₄(OCH₂CH₂O)₆ with an expected cordierite ceramic yield of 40%, which is close to that observed. The XRD pattern of the precursor is illustrated in FIG. 5.

Likewise similar syntheses with BaO:2SiO₂:2Al(OH)₃ or SrO:2SiO₂:2Al(OH)₃ ratio gives a barium aluminosilicate precursor with a suggested formula of:

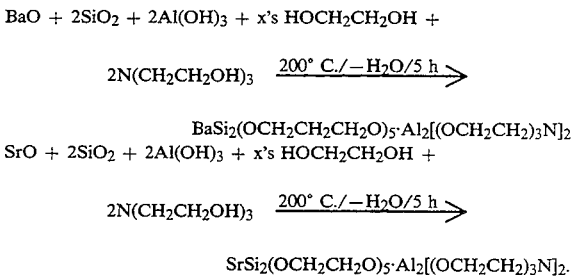

EXAMPLE 13

Dissolution of a Monopotassium Aluminosilicate (KAlSiO₄) Precursor

Potassium Hydroxide (5.13 g, 82 mmol of 95% KOH) was added to a flask with 50 mL of ethylene glycol. The slurry was heated under N₂ until all of the KOH dissolved. 7.6 g of Al(OH)₃.xH₂O (54.8% as Al₂O₃, 82.3 mmol) was introduced to a clean flask. The dissolved KOH solution was then added to this flask. An additional 100 mL of glycol was used to ensure that all of the KOH was washed into the flask. The resulting solution was brought to reflux under N₂ for 1 hour and the solution was allowed to distill until all of the Al(OH)₃ had dissolved (≈1 h) as evidenced by a clear solution.

The solution was allowed to cool and 5.0 g of fumed SiO₂ (82 mmol) was added. The solution was again refluxed. Ethylene glycol was distilled off slowly over a period of 10 h. The object of the distillation was to remove product water formed from the anticipated reaction of the potassium glyocolato aluminum with SiO₂. At the end of 10 h, the solution remained opaque as the SiO₂ powder did not react under conditions where it would usually react in the space of 20 min, if excess akali base was added.

EXAMPLE 14

Dissolution of a Monopotassium Aluminosilicate (KalSiO₄) Precursor

The unreacted final solution from Example 13 was then mixed with 0.97 equivalents (12 g, 80 mmol) of TEA and heated to distill for 1 h. The opaque solution turned clear during the 1 h reflux. The resulting preceramic polymer can be used to make Ka/SiO₄ based zeolites or amorphous ceramic products or crystalline non-zeolite products.

MASS SPECTRAL RESULTS

Fast atom bombardment (FAB) analyses of the above reaction products results in the production of ions and some fragmentation results.

TEA (F.W. 149.19) by itself gives the fragmentation pattern =
M+1, m/e=150 (100), M−1 m/e 148 (58), M−17, m/e=132, M−31, m/e=118 ( )

For silatrane derivatives $(N(CH_2CH_2O)_3Si-R)$ will expect fragmentation pattern as follows:
$N(CH_2CH_2O)_3Si+(174.25)=174$
$HN(CH_2CH_2O)_3SiOCH_2CH_2OH(236.232)=236$
$HN(CH_2CH_2O)SiN(CH_2CH_2O)_3H_2=323$ FAB analysis of product of Example 2 with ≈ < equivalent of TEA (Si001)). Note that valves in ( ) are intensities.
Species present:

| | | |
|---|---|---|
| $N(CH_2CH_2O)_3Si^+ =$ | 174 (100) | |
| $R = OCH_2CH_2OH$ | 236 (8) | |

FAB analysis of product of Example 1.
Species present:

| | |
|---|---|
| $N(CH_2CH_2O)_3H_4^+ =$ | 150 (100) |
| $N(CH_2CH_2O)_3H_2^+ =$ | 148 (58) |
| $N(CH_2CH_2O)_3Si^+ =$ | 174 (33) |
| $HN(CH_2CH_2O)_3SiOCH_2CH_2OH236$ | 236 (12) |
| $HN(CH_2CH_2O)_3SiNOCH_2CH_2N(CH_2CH_2O)_2H_2 =$ | 323 |
| $HN(CH_2CH_2O)_3SiNOCH_2CH_2N(CH_2CH_2O)_2CH_2 =$ | 291 (8) |
| $R = N(CH_2CH_2O)_3H_2 =$ | 323 (35) |

FAB analysis of product of Example 4 (Si003)
No signal.
FAB anaylsis of product of Example 4 after adding a large excess of TEA (Si004, Si003 with TEA).
Species Present:

| | | |
|---|---|---|
| $N(CH_2CH_2O)_3H_2^+ =$ | 148 | (6) |
| $N(CH_2CH_2O)_3H_4^+ =$ | 150 | (52) |
| $N(CH_2CH_2O)_3Si^+ =$ | 175 | (70) |
| $R = OCH_2CH_2OH, H$ | 236 | (100) |
| $R = N(CH_2CH_2O)_3H_2 =$ | 323 | (8) |
| $HOCH_2CH_2N(CH_2CH_2O)_2SiRR'$ | | |
| $R = OCH_2CH_2OH$ | | |
| $R' = N(CH_2CH_2O)_3H_2 =$ | 385 | (13) |

$N(CH_2CH_2O)_3Si-OCH_2CH_2O-Si-(OCH_2CH_2)_3N = 408$ not seen $N(CH_2CH_2O)_3Si-OCH_2CH_2O-Si-(OCH_2CH_2OH)(OCH_2CH_2)_2NCH_2CH_2OH + H$
= 471 (21)
496

$HOCH_2CH_2N(CH_2CH_2O)_2Si(OCH_2CH_2OH)OCH_2CH_2N(CH_2CH_2O)_2Si(OCH_2CH_2)_3N(H_2)$
620 (3)

$H_4[N(CH_2CH_2O)_3Si(OCH_2CH_2O)]_3 =$

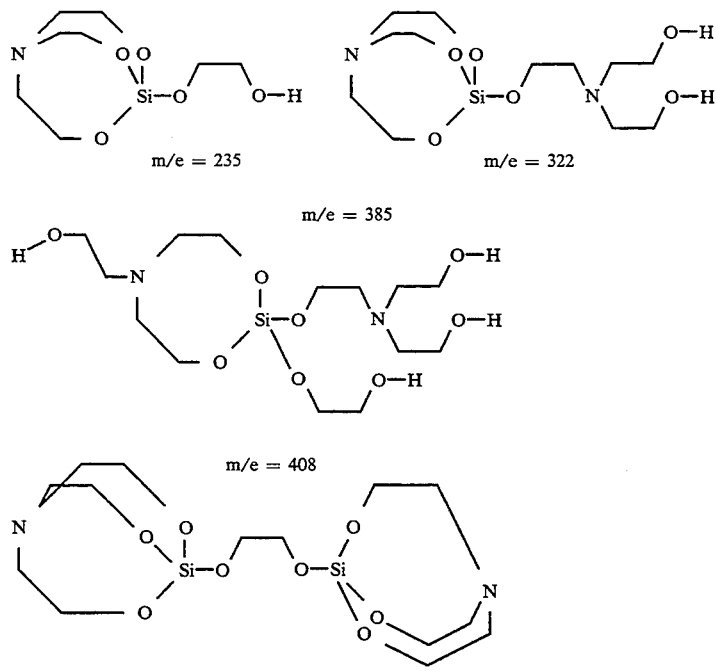

-continued

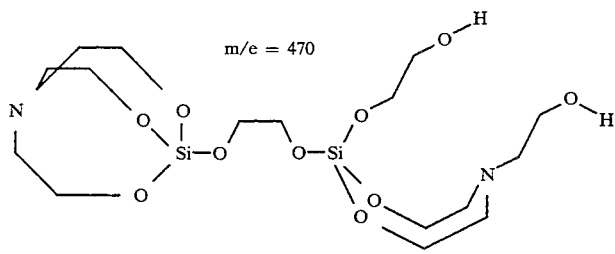
m/e = 470

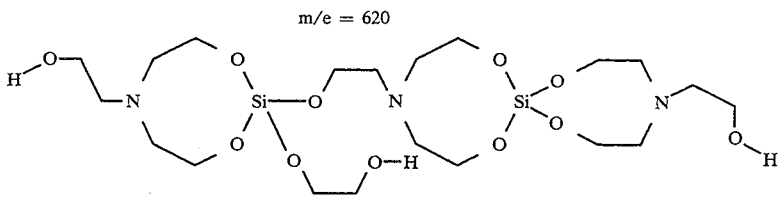
m/e = 620

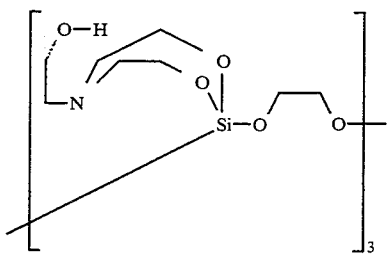

m/e = 706 and/or

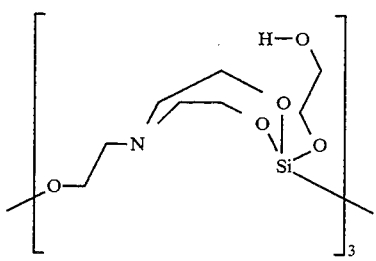

m/e = 706

In the above instances, the number 3 could now be determined to be any larger number and thus indicates the type of polymer structures that form.

Al Mass Spectral Results:

Fast atom bombardment (FAB) results in the production of ions and some fragmentation results.

Example 9 with excess TEA (AL 001)

Species Present

| | | |
|---|---|---|
| $N(CH_2CH_2OH)_2CH_2^+ =$ | 118 | (94) |
| $N(CH_2CH_2OH)_2CH_2CH_2^+ =$ | 132 | (77) |
| $N(CH_2CH_2O)_3H_2^+ =$ | 148 | (58) |
| $N(CH_2CH_2O)_3H_4^+ =$ | 150 | (100) |
| $N(CH_2CH_2O)_3Al^+$ (M − 1) = | 172 | (40) |
| $N(CH_2CH_2O)_3AlH^+$ (M + 1) = | 174 | (39) |
| $CH_2CH_2N(CH_2CH_2O)_2AlOCH_2CH_2O^+ =$ | 216 | (22) |
| $HOCH_2CH_2N(CH_2CH_2O)_2AlOCH_2CH_2OH$ (235.17) = | 235 | |
| $HN(CH_2CH_2O)_2AlOCH_2CH_2N(CH_2CH_2O)_2Al$ | 303(36) | |
| $OCH_2CH_2N(CH_2CH_2O)_2AlOCH_2CH_2N(CH_2CH_2O)_2AlH$ | 347 | (32) |

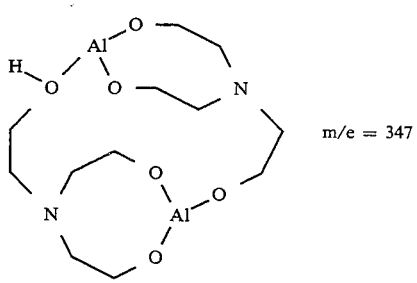
m/e = 347

—$OCH_2CH_2OAl(OCH_2CH_2N(CH_2CH_2O)_2Al)_2$-(433.33)     433(15)

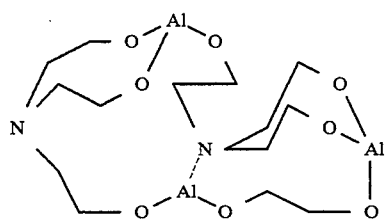
m/e = 433
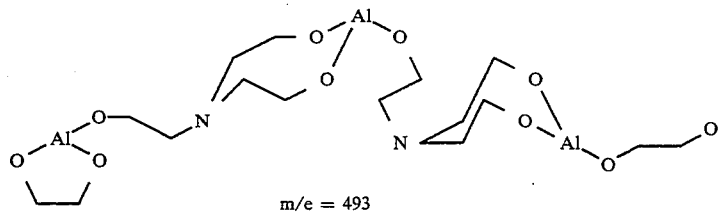
m/e = 493
[OCH$_2$CH$_2$N(CH$_2$CH$_2$O)$_2$Al]$_3$ = Al$_3$C$_{18}$H$_{36}$N$_3$O$_9$    519.44
562(11)
—OCH$_2$CH$_2$OAl(OCH$_2$CH$_2$CH$_2$N(CH$_2$CH$_2$O)$_2$Al)$_3$-(606.48)    606(16)
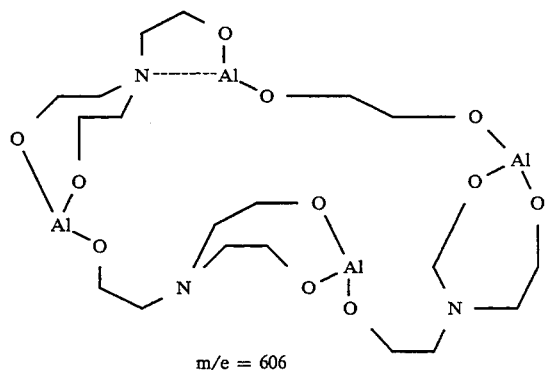
m/e = 606
[OCH$_2$CH$_2$N(CH$_2$CH$_2$O)$_3$Al]$_4$    692.60.
These products indicate that two types of aluminum polymers are formed. One is simply based on TEA ligands and looks like:
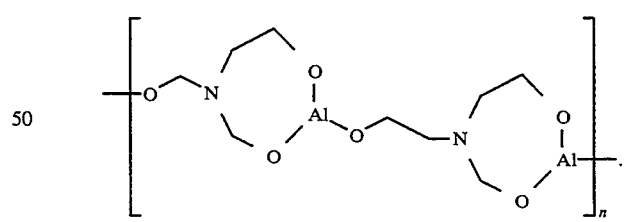
The other has ethylene glycol groups and contains structural units such as:
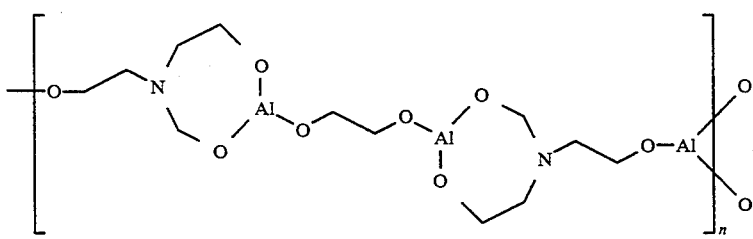

Example 8, Mullite Experiments with TEA
Species present:

| | |
|---|---|
| $N(CH_2CH_2OH)_2CH_2^+$ = | 118 (100) |
| $N(CH_2CH_2OH)_2CH_2CH_2^+$ = | 132 (82) |
| $N(CH_2CH_2O)_3H_2^+$ = | 148 (27) |
| $N(CH_2CH_2O)_3H_4^+$ = | 150 (92) |
| $N(CH_2CH_2O)_3Al^+(M-1)$ = $N(CH_2CH_2O)_3AlH^+(M+1)$ or | 172 (42) |
| $N(CH_2CH_2O)_3Si^+$ = | 174 (56) |
| $CH_2CHN(CH_2CH_2O)_2AlOCH_2CH_2O^+$ = | 216 (30) |
| | 234 (22) |
| $HOCH_2CH_2N(CH_2CH_2O)_2AlOCH_2CH_2OH(235.17)$ = | 235 |
| | 240 (20) |

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A neutral or mixed neutral/ionic polymetallooxane comprising the moiety:

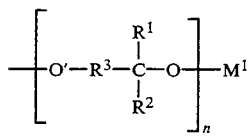

wherein n is 2 or 3 when $M^1$ is Al or Ga, and 3 or 4 when $M^1$ is Si, Ge, or Sn;

$M^m$ is selected from the group consisting of tetravalent Si, tetravalent Ge, tetravalent Sn, trivalent Al, and trivalent Ga;

$R^1$ and $R^2$ are independently selected from the group consisting of H, OH, $C_{1-8}$ alkyl, $C_{1-6}$ alkoxy, $C_{2-8}$ alkene, $C_{6-12}$ aryl, $C_{1-8}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane and combinations thereof;

O' is bonded to $M^1$, $M^2$ or H, wherein $M^2$ is selected from the group consisting of Si, Ge, Sn, Al and Ga, an ammonium species, and a Group I or II metal of the Periodic Table; wherein when O' is bonded to $M^1$, n is 2 when $M^1$ is Al or Ga, and n is 3 when $M^1$ is Si, Ge, or Sn; and wherein at least one O' is bonded to $M^2$; and $R^3$ is independently selected from the group consisting of $(CR_2)_y$, $(CR_2CR_2)_yN(CR_2)_y$, $(CR_2CR_2)_yNR(CR_2)_y[(CR_2CR_2)_yO]_y$—$(CR_2)_y$, and combinations thereof wherein R is selected from the group consisting of H, OH, $C_{1-8}$ alkyl, $C_{1-6}$ alkoxy, $C_{2-8}$ alkenyl, $C_{6-12}$ aryl, $C_{1-18}$ hydroxyalkyl, $C_{1-8}$ thioalkyl, $C_{2-12}$ alkoxyalkyl, $C_{4-20}$ heteroaromatic, $C_{1-10}$ alkylsilane, $C_{1-10}$ alkylsiloxane and combinations thereof, and where y is a number from 1 to 10, and wherein said polymetallooxane contains at least one $M^2$.

2. The polymetallooxane composition of claim 1, further comprising the heterocyclic moiety

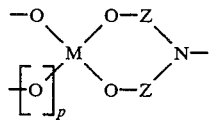

wherein M is Al, Ga, Si, Ge or Sn; and wherein when M is Al or Ga, p is 0, and when M is Si, Ge or Sn, p is 1, wherein Z is the residue of an amine reactant.

3. The polymetallooxane of claim 1 where:
n is 3 or 4;
$M^1$ is Si; and
O' is bonded to $M^1$ (4-n) times.

4. The polymetallooxane of claim 1 where:
n is 2 or 3;
$M^1$ is Al; and
O' is bonded to $M^1$ (3-n) times.

5. The polymetallooxane of claim 1 where:
$R^3$ contains at least one nitrogen atom.

6. The polymetallooxane of claim 1 where all $M^1$ atoms are Si.

7. The polymetallooxane of claim 1 where $M^2$ is a group I metal.

8. The polymetallooxane of claim 1 where $M^2$ is a group II metal.

9. The polymetallooxane of claim 1 where all $M^1$ atoms are Al.

10. The polymeric composition of claim 2 wherein the reactant used to form Z is a polyol.

11. The polymeric composition of claim 2 wherein the reactant used to form Z is an alkanolamine.

* * * * *

UNITED STATES PATENT AND TRADEMARK OFFICE
CERTIFICATE OF CORRECTION

PATENT NO. : 5,418,298

DATED : May 23, 1995

Page 1 of 4

INVENTOR(S) : Richard M. Laine; Brian L. Mueller; Tom Hinklin

It is certified that error appears in the above-indentified patent and that said Letters Patent is hereby corrected as shown below:

Title Page, under "OTHER PUBLICATIONS"

Under the first *Frye* reference, after "Mar. 11, 1970", replace "pp. 1205 & 1210" with -- pp. 1205-1210 --.

The *Blohowiak* reference appears twice. Delete second occurrence. On line 2 of the *Blohowiak* reference, insert "," prior to "Inorg."

In Column 1, line 6, after "DAAL04-91-C-0068, replace "awaded" with -- awarded --.

In Column 3, line 61, after "O' " insert -- - -- (hyphen).

In Column 3, line 62, after "O' " insert -- - -- (hyphen).

In Column 4, line 3, replace "C1-10" with -- $C_{1-10}$ --.

In Column 4, line 3, after "thereof" delete "." (period).

In Column 4, line 18, after "z" replace "us" with -- is --.

In Column 5, line 27, before "also" insert -- can --.

In Column 6, line 41, delete "monothyl" and insert therefor -- monoethyl --.

UNITED STATES PATENT AND TRADEMARK OFFICE
CERTIFICATE OF CORRECTION

PATENT NO. : 5,418,298

DATED : May 23, 1995

INVENTOR(S) : Richard M. Laine; Brian L. Mueller; Tom Hinklin

It is certified that error appears in the above-indentified patent and that said Letters Patent is hereby corrected as shown below:

In Column 7, line 16, after "all" replace "heterocycle" with -- heterocyclic --.

In Column 8, line 1, after "z" replace "us" with -- is --.

In Column 8, line 19, after "reaction of the" replace "danging" with -- dangling --.

In Column 8, line 62, replace "promotespolymetallooxane" with
    -- promotes polymetallooxane --.

In Column 8, line 63, replace "heterocycle" with
    -- heterocyclic -- .

In Column 8, line 63, replace "discribed" with
    -- described --.

In Column 13, line 9, after "distill" replace "of" with
    -- off --.

In Column 13, line 33, after "remaining" replace "E" with
    -- EG --.

In Column 13, line 42, after "distill" replace "of" with
    -- off --.

In Column 13, line 55, after ". . .OH)$_3$, (", replace
    "$\mu$OCH$_2$. . ." with -- $\mu$-OCH$_2$. . . --.

In Column 13, line 58, replace "$\mu$OCH$_2$" with -- $\mu$-OCH$_2$ --.

UNITED STATES PATENT AND TRADEMARK OFFICE
CERTIFICATE OF CORRECTION

PATENT NO. : 5,418,298  
DATED : May 23, 1995  
INVENTOR(S): Richard M. Laine; Brian L. Mueller; Tom Hinklin It is certified that error appears in the above-indentified patent and that said Letters Patent is hereby corrected as shown below:

In Column 13, line 60, after "($OCH_2CH_2O$" insert -- ) -- (paren).

In Column 14, line 4, after "and" replace "analyzied" with -- analyzed --.

In Column 14, line 23, after "distill", replace "of" with -- off --.

In Column 14, line 40, after "distill", replace "of" with -- off --.

In Column 14, line 57, after "distill", replace "of" with -- off --.

In Column 15, line 5, after "distill", replace "of" with -- off --.

In Column 17, line 18, after "that", replace "valves" with -- values --.

UNITED STATES PATENT AND TRADEMARK OFFICE
CERTIFICATE OF CORRECTION

PATENT NO. : 5,418,298
DATED : May 23, 1995
INVENTOR(S) : Richard M. Laine; Brian L. Mueller; Tom Hinklin It is certified that error appears in the above-indentified patent and that said Letters Patent is hereby corrected as shown below:

In the Claims

In Column 23, line 36, before "is selected" replace "$M^m$" with -- $M^1$ --.

Signed and Sealed this

Twenty-first Day of May, 1996

Attest:

BRUCE LEHMAN

Attesting Officer     Commissioner of Patents and Trademarks